United States Patent
Wang et al.

(10) Patent No.: US 12,312,268 B2
(45) Date of Patent: May 27, 2025

(54) MANGANESE-OXIDIZING FUNGUS AND USES THEREOF

(71) Applicant: TONGJI UNIVERSITY, Shanghai (CN)

(72) Inventors: Mei Wang, Shanghai (CN); Zuxin Xu, Shanghai (CN); Bin Dong, Shanghai (CN)

(73) Assignee: TONGJI UNIVERSITY, Shanghai (CN)

( * ) Notice: Subject to any disclaimer, the term of this patent is extended or adjusted under 35 U.S.C. 154(b) by 774 days.

(21) Appl. No.: 17/324,131

(22) Filed: May 19, 2021

(65) Prior Publication Data

US 2022/0220016 A1     Jul. 14, 2022

(30) Foreign Application Priority Data

Jan. 14, 2021   (CN) .......................... 202110048920.0

(51) Int. Cl.
| | | |
|---|---|---|
| *C02F 3/34* | (2023.01) | |
| *B09C 1/10* | (2006.01) | |
| *C12N 1/14* | (2006.01) | |
| *C12R 1/645* | (2006.01) | |
| *C02F 101/20* | (2006.01) | |

(52) U.S. Cl.
CPC .............. *C02F 3/347* (2013.01); *B09C 1/105* (2013.01); *C12N 1/145* (2021.05); *C02F 2101/206* (2013.01); *C12R 2001/645* (2021.05)

(58) Field of Classification Search
CPC .... C02F 3/347; C02F 2101/206; B09C 1/105; C12N 1/145; C12R 2001/645
See application file for complete search history.

(56) References Cited

U.S. PATENT DOCUMENTS 4,293,333 A  *  10/1981  Drobot ...................... C02F 3/34
                                                    423/100

FOREIGN PATENT DOCUMENTS

CN       112094766       12/2020

OTHER PUBLICATIONS

Cahyani et. al. Phylogenetic positions of Mn2+-oxidizing bacteria and fungi isolated from Mn nodules in rice field subsoils. Biol Fertil Soils 45:337-346. (Year: 2009).*
Wang et. al. An efficient manganese-oxidizing fungus *Cladosporium halotolerans* strain XM01: Mn(II) oxidization and Cd adsorption behavior. Chemosphere 287 132026 (Year: 2022).*
Manganese—DCCEEW https://www.dcceew.gov.au/environment/protection/npi/substances/fact-sheets/manganese-compounds. (Year: None) (Year: None).*
Yue Zhang et al., "A novel manganese oxidizing bacterium—*Aeromonas hydrophila* strain DS02: Mn(II) oxidization and biogenic Mn oxides generation," Journal of Hazardous Materials, vol. 367, Apr. 5, 2019, pp. 539-545.
Wenwei Tanga et al., "DGGE diversity of manganese mine samples and isolation of a *Lysinibacillus* sp. efficient in removal of high Mn (II) concentrations," Chemosphere, vol. 165, Dec. 2016, pp. 277-283.

* cited by examiner

*Primary Examiner* — Liam Royce
(74) *Attorney, Agent, or Firm* — JCIP GLOBAL INC.

(57) ABSTRACT

A fungus having manganese oxidation capacity is provided. The fungus can oxidize $Mn^{2+}$ in a water body into a water-insoluble manganese oxide; and the $Mn^{2+}$ oxidizing fungus is *Cladosporium* sp. XM01 strain with the accession number of CGMCC NO. 21083. The *Cladosporium* sp. XM01 strain is used to oxidize $Mn^{2+}$ in a natural water body, and has stable operation within a range of room temperature (15-30° C.) and a range of neutral pH (6.0-7.5) and high $Mn^{2+}$ oxidation efficiency; moreover, the XM01 strain may oxidize $Mn^{2+}$ cyclically, thereby achieving the in-situ remediation of water bodies or soils polluted by heavy metals or trace organic substances. The manganese oxides generated through oxidization in the growth process of the strain have a good application potential in sewage treatment, water environment restoration, soils and other fields.

2 Claims, 8 Drawing Sheets
Specification includes a Sequence Listing.

SEQUENCE LISTING

<160> NUMBER OF SEQ ID NOS: 1

<210> SEQ ID NO 1
<211> LENGTH: 557
<212> TYPE: DNA
<213> ORGANISM: Cladosporium sp. XM01

<400> SEQUENCE: 1

```
ttccgttggg ggggcctgcg gagggatcat tacaagttga ccccggccct cgggccggga      60
tgttcacaac cctttgttgt ccgactctgt tgcctccggg gcgaccctgc ctccgggcgg     120
gggccccggg tggacatttc aaactcttgc gtaactttgc agtctgagta aatttaatta     180
ataaattaaa actttcaaca acggatctct tggttctggc atcgatgaag aacgcagcga     240
aatgcgataa gtaatgtgaa ttgcagaatt cagtgaatca tcgaatcttt gaacgcacat     300 tgcgcccct ggtattccgg ggggcatgcc tgttcgagcg tcatttcacc actcaagcct     360
cgcttggtat tgggcgacgc ggtccgccgc gcgcctcaaa tcgaccggct gggtctttcg     420 tccctcagc gttgtggaaa ctattcgcta aagggtgccg cgggaggcca cgccgtaaaa     480 caacccatt tctaaggttg acctcggatc aggtagggat acccgctgaa cttaagcata     540
tcaaaaggcc ggaggaa                                                    557
```

MANGANESE-OXIDIZING FUNGUS AND USES THEREOF

CROSS-REFERENCE TO RELATED APPLICATION

This application claims the priority benefit of China Application No. 202110048920.0, filed on Jan. 14, 2021. The entirety of the above-mentioned patent application is hereby incorporated by reference herein and made a part of this specification.

BACKGROUND

Technical Field

The present disclosure relates to the technical field of environmental microorganisms, and in particular to a manganese-oxidizing fungus and uses thereof.

Description of Related Art

In recent years, biological manganese oxides have good adsorption and oxidation capacity; compared with chemosynthetic manganese oxides, biological manganese oxides have weak crystallization, small grain size, high valence state of Mn, and have many octahedral cavities in the structure thereof. Therefore, biological manganese oxides have stronger adsorption capacity, oxidation capacity and other surface activity. Moreover, biological manganese oxides are produced in eco-friendly conditions without the excessive use of energy sources. Therefore, the biological manganese oxide may be regarded as a cost-effective and environment-friendly material, and used for the remediation of the polluted environment.

The formation mechanism of manganese oxides may be divided into a chemical origin and a biogenic origin. Comparatively speaking, the biogenic origin believes that microorganisms are mainly mediated by Mn oxidization process in natural world; and the biologically mediated Mn oxidization rate is several times faster than the chemo-catalysis rate, and even tens of thousands times above. Up to now, numerous types of microorganisms have been found to have Mn oxidation capacity; and these manganese oxides are widely distributed in the wild, and manganese-oxidizing bacteria in the continental ecosystem mainly exist in soils, deposits, water pipes, desert varnish, caves and ores. Manganese-oxidizing bacteria in freshwater system mainly exist in hot springs of fresh water, rivers, streams, ponds, Mn-enriched surface films in shallow lakes, iron-manganese concretion, deposits in fresh water, aerobiotic/anoxic interfaces of bays.

Bacteria and fungi are regarded as important Mn transforming agents to oxidize $Mn^{2+}$ into Mn (III, and IV) and to produce nanoscale biological manganese oxides having poor crystallization. Currently, Mn-related microbial oxidization is mainly focused on bacteria, including the removal of heavy metals in a polluted environment by a manganese-oxidizing bacterium, structure features of a product formed by manganese oxidization via a manganese-oxidizing bacterium, a manganese oxidation mechanism of a manganese-oxidizing bacterium, and the like. For example, a patent CN112094766 A discloses a manganese oxidizing bacterium; while researchers have scarcely known about the contribution of manganese-oxidizing fungi to the transformation of manganese oxides in the environment and influences thereof on the fate of inorganic substances in the environment. However, compared with bacteria, filamentous fungi are more superior to oxidizing manganese in the environment: (1) the growing ability of fungi within a wide pH range; (2) the resistance of fungi to high-concentration toxic metals and organic pollutants. Many fungi capable of oxidizing manganese (II) can be separated from soils, rock surfaces, sediments, sludge, fresh water and other environment, including Acridine, *Alternaria, Cladosporium*, Anapiculatisporites, *Curvularia, Penicillium* and the like. The studies on manganese-oxidizing fungi are mainly focused on *Acremonium* sp. and *Phanerochaete chrysosporium*. By biosorption and oxidization of these manganese-oxidizing fungi, manganese ions Mn (II) in water are allowed to form biological manganese oxides. These findings bring a brand-new idea for the biological removal of manganese, oxidization and adsorption of pollutants in water (such as, heavy metals, and trace organic pollutants). Therefore, the process is a novel biological treatment method of manganese-containing waste water, and has a broad application prospect. Nutritional deficiency and competitive effects of microorganisms are present in natural hydrological conditions, which will influence the survival and manganese oxidation activity of strains. Therefore, it is very important to seek manganese-oxidizing strains suitable for natural hydrological conditions.

SUMMARY

The objective of the present disclosure is to provide a manganese-oxidizing fungus and uses thereof, thus solving the above problems. The manganese-oxidizing fungus in this present disclosure belongs to *Cladosporium* sp., and can be suitable for complex natural water bodies and exert manganese-oxidizing effects, and has very good application prospects.

The manganese-oxidizing fungus disclosed in the present disclosure has high $Mn^{2+}$ oxidization efficiency within a scope of temperature (15-30° C.) and a scope of neutral pH (6.0-7.5).

The objective of the present disclosure is achieved by the following technical solution:

A manganese-oxidizing fungus is provided, and the manganese-oxidizing fungus is *Cladosporium* sp. XM01, and has been preserved in China General Microbiological Culture Collection Center (accession number: CGMCC NO. 21083).

The manganese-oxidizing fungus of this present disclosure is obtained by domesticating, separating and purifying the soil derived from the nearby Xiangtan Manganese Mine of Hunan Province.

ITS rRNA sequencing results of XM01 in the present disclosure is led to GenBank database of NCBI for homology comparison. The results indicate that the maximum similar strain is *Cladosporium* sp. having a similarity of 99%. Therefore, the strain can be judged to be *Cladosporium* sp. and named *Cladosporium* sp. XM01.

The manganese-oxidizing fungus in this present disclosure grows and has $Mn^{2+}$ oxidation activity under the conditions that a temperature range is 15-30° C., a pH range is 6.0-7.5, and preferably 7, and a $Mn^{2+}$ concentration is not higher than 800 μM. $Mn^{2+}$ removal rate is up to 99.9% and manganese oxidation rate is up to over 80%.

The manganese-oxidizing fungus in this present disclosure lives in a non-sterilized water body or a solid matrix and exerts $Mn^{2+}$ oxidization activity.

The manganese-oxidizing fungus in this present disclosure is used in the treatment of toxic metallic elements or trace organic pollutants to remove $Mn^{2+}$ in a water body or a solid matrix, or used in a preparation of a microbial agent, or used in a preparation of an adsorbent for metallic elements. The water body includes industrial wastewater, domestic wastewater, underground water and tap water; and the solid matrix includes a soil and a deposit.

A gene sequence of a manganese-oxidizing fungus, is shown in SEQ ID NO.1.

A microbial agent, includes a *Cladosporium* sp. XM01 strain with the accession number of CGMCC NO. 21083 as an active ingredient.

A method for removing $Mn^{2+}$ from a water body or a solid matrix, including the following steps of: inoculating the manganese-oxidizing fungus or a microbial agent including the manganese-oxidizing fungus onto a water body or a solid matrix for culturing for a proper period under the conditions of 15-30° C. and pH=6.0-7.5, where the water body includes industrial wastewater, domestic wastewater, underground water and tap water; and the solid matrix includes a soil and a deposit.

Compared with the prior art, the present disclosure has the following advantages:

(1) Low manganese oxidization cost: during the overall oxidization, a conventional fungal PYG medium is used to achieve high-density activization of a strain; moreover, in later oxidizing process, trace trophic factors can achieve better oxidization effect without complex and expensive drugs and apparatus.

(2) Great application potential: the independently screened manganese-oxidizing strain has better $Mn^{2+}$ oxidation capacity; the high-valent insoluble manganese oxides produced have a higher value of research in the aspects, such as catalytic oxidation, degradation, adsorption of waterborne pollutants (e.g., heavy metals, and organic pollutants); therefore, the strain is considered to be used in remediation and remediation of water environment and soils.

DESCRIPTION OF THE EMBODIMENTS

Figure 1:
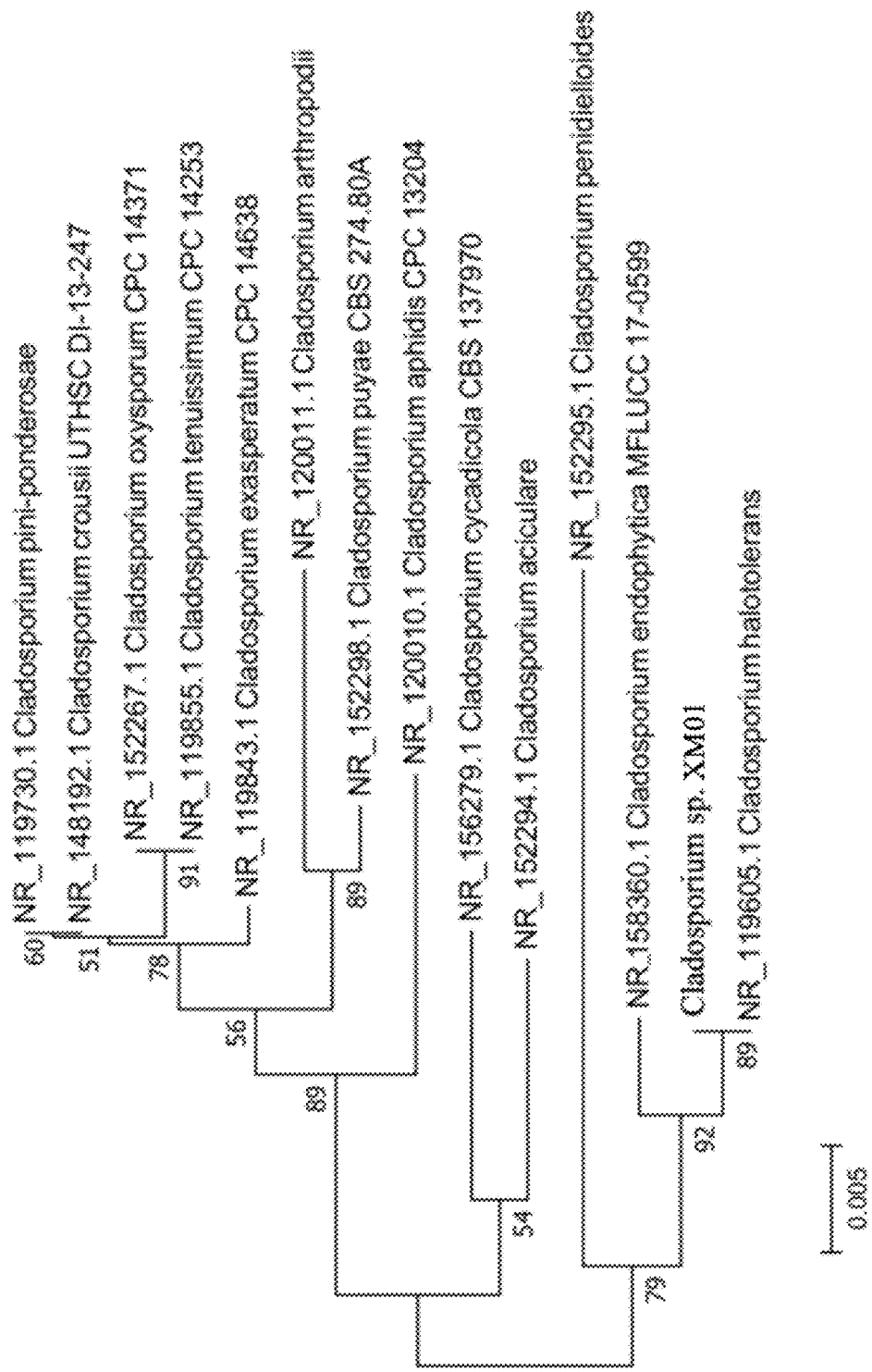
FIG. 1 shows a phylogenetic dendrogram of *Cladosporium* sp. XM01 in this present disclosure based on ITS rRNA genes.
Figure 2:
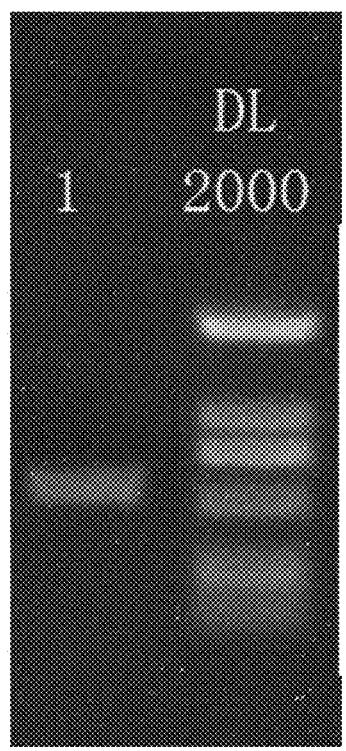
FIG. 2 shows electrophoretogram of *Cladosporium* sp. XM01 in this present disclosure (DL2000 band distribution: 2000, 1000, 750, 500, 250, and 100 bp).

The present disclosure will be further described in details with reference to detailed examples; and those skilled in the art should understand that the present disclosure is not limited to these detailed examples.

Unless otherwise specified, methods in the following examples should be conventional methods; and the reagents used therein are conventional reagents available in the market.

Example 1

Isolation and Purification of a Manganese-Oxidizing Fungus *Cladosporium* sp. XM01

*Cladosporium* sp. XM01 was obtained by sampling, domesticating, separating and purifying the soil derived from the manganese ore stacked in Xiangtan Manganese Mine of Hunan Province. Specific steps were as follows:

(1) Preliminary screening: black brown soil was collected from the nearby Xiangtan Manganese Mine of Hunan Province; and 2 g soil was taken and added to an HAY medium sterilized by high temperature (0.246 g/L sodium acetate; 0.15 g/L yeast powder; 0.05 g/L magnesium sulfate heptahydrate; 5 mg/L dipotassium phosphate; 2 mL/L mineral salts; where per liter of mineral salts included the ingredients below: 3.7 g calcium chloride dihydrate; 0.44 g zinc sulfate heptahydrate; 0.29 g sodium molybdate dihydrate; 2.5 g boric acid; 5 mg copper sulfate pentahydrate; and 1.0 g ferric chloride hexahydrate) in a laboratory to make the content of $MnCl_2$ being 200 μM; a buffer solution in the medium was HEPES having a final concentration of 20 mM and pH of 7.0; where the $MnCl_2$ solution and HEPES buffer solution were filtered by a 0.22 μm filter membrane and sterilized for addition. The above soil was domesticated for 7 d every time on a 170 rpm table in dark place at 25° C., after the domestication, 5 mL domesticated fungal solution was taken and added onto a freshly-prepared 45 mL HAY medium for continuous domestication for 4 times in total.

(2) Secondary screening: after the domestication, the fungal solution was diluted $10^{-1}$ to $10^{-7}$ folds by sterilized tap water; 0.1 mL diluent was respectively taken and coated on a solid medium containing 100 μM $Mn^{2+}$ (prepared by adding 2% agar to the above liquid HAY culture medium) for isolation, and cultured in the dark at 25° C. After obvious colonies grew on the medium, a single colony forming brown substances thereon was picked and marked out for isolation and purification. A strain having stronger manganese oxidation capacity was determined by surveying the growth rate and $Mn^{2+}$ oxidation rate of these fungi.

(3) Liquid culture conditions of the *Cladosporium* sp. XM01 strain: a 150 mL HAY medium was added to a 250 mL conical flask, and an HEPES buffer solution having a final concentration of 20 mM and a pH value of 6.0-8.0 was added; and the table was configured at 170 rpm and 15-30° C. The strain cells were collected by centrifugation for 10 min at 3000-5000 r/min.

Example 2

Molecular Biological Identification of *Cladosporium* sp. XM01

*Cladosporium* sp. XM01 was extracted by a fungal genome kit (purchased from Omega, Code no. D3390-02), and subjected to PCR amplification by using universal primers ITS1(TCCGTAGGT GAACCTGCGG) and ITS4 (TCCTCCGCTTATTGATATGC) for fungi ITS rRNA genes. PCR reaction system:

| 10 × Ex Taq buffer | 2.0 μl |
|---|---|
| 5 u Ex Taq | 0.2 μl |

-continued

| | |
|---|---|
| 2.5 mM dNTP Mix | 1.6 μl |
| 5 p Primer 1 | 1 μl |
| 5 p Primer 2 | 1 μl |
| DNA | 0.5 μl |
| ddH$_2$O | 13.7 μl |
| Total volume | 20 μl |

PCR experiments were performed using the following program: initial denaturation at 95° C. for 5 min, followed by 25 cycles of denaturation at 95° C. for 30 s, primer annealing at 56° C. for 30 s and extension at 72° C. for 30 s. A final long extension was at 72° C. for 10 min.

Samples were sequenced via the amplified PCR product by Majorbio. Sequences obtained by sequencing were as shown in SEQ ID NO.1, and were compared to the sequences in database by BLAST on line; sequences having greater than 97% similarity were selected as reference sequences; and a phylogenetic tree of fungal system was constructed by Neighbor-Joining with Mega4.0 software (FIG. 1).

Example 3

Scanning Electron Microscope (SEM) and Energy Dispersive X-Ray Detector (EDX) of *Cladosporium* sp. XM01

Figure 3A:
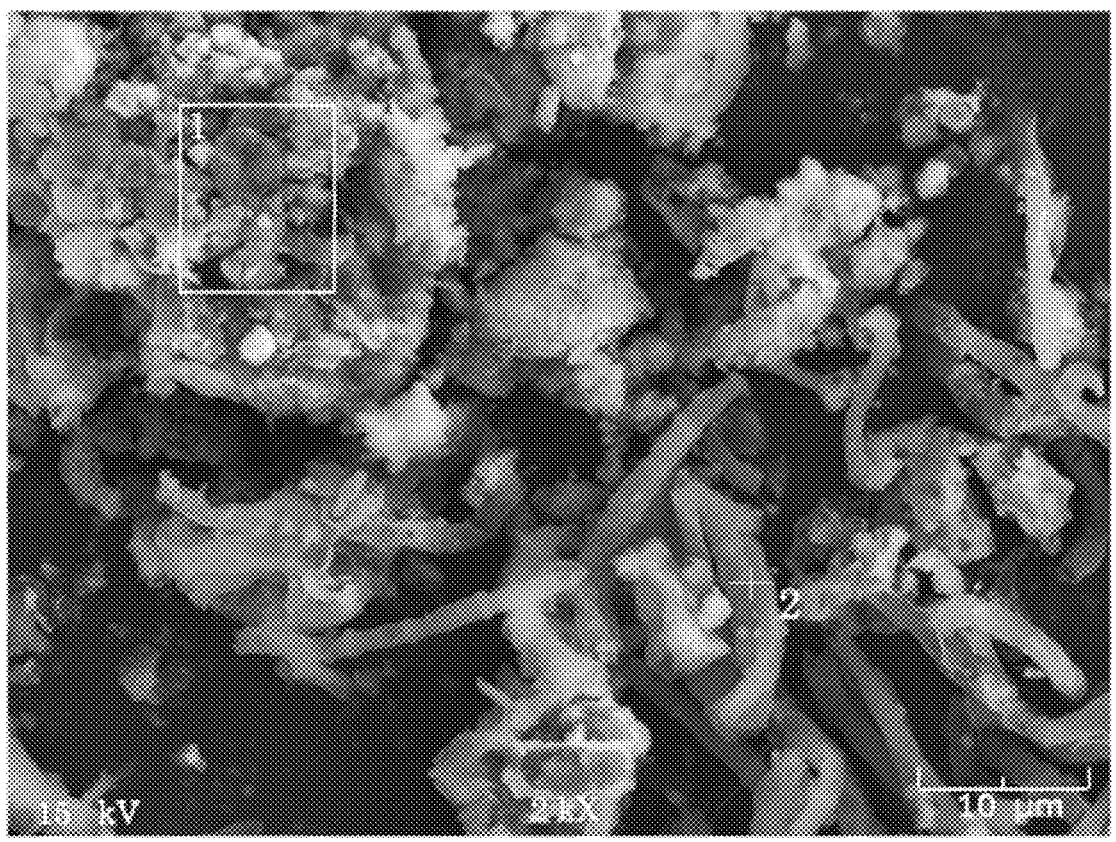
FIGS. 3a-3c shows a SEM graph (2kX) of biological manganese oxides produced by 10 *Cladosporium* sp. XM01 in this present disclosure and energy spectrum analysis corresponding to markers, where the box portion denotes the markers (FIGS. 3b and 3c, FIG. 3b denotes marker 1 and FIG. 3c denotes marker 2).
Figure 3B:
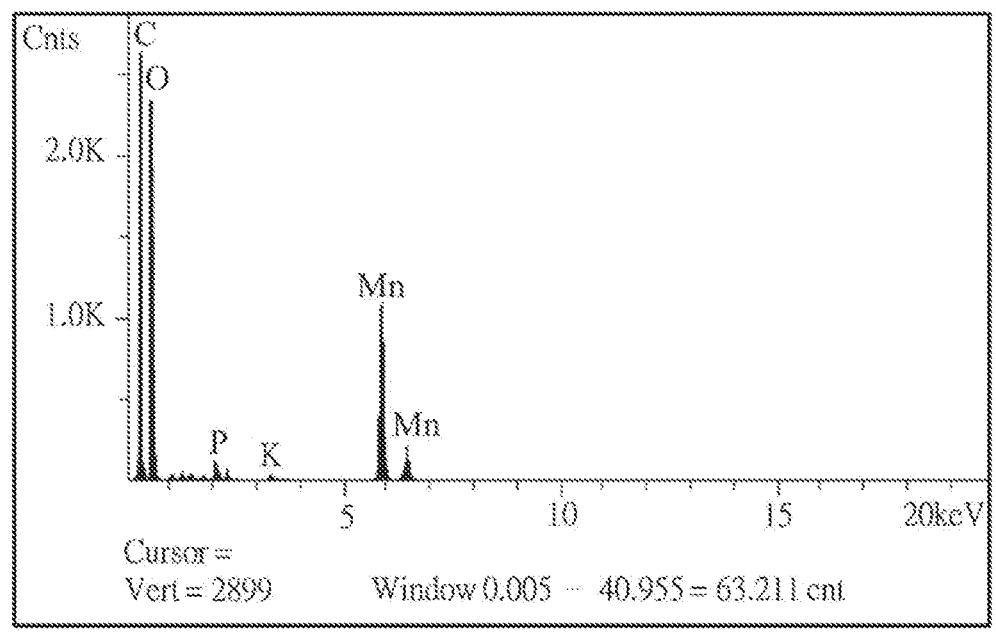
Figure 3C:
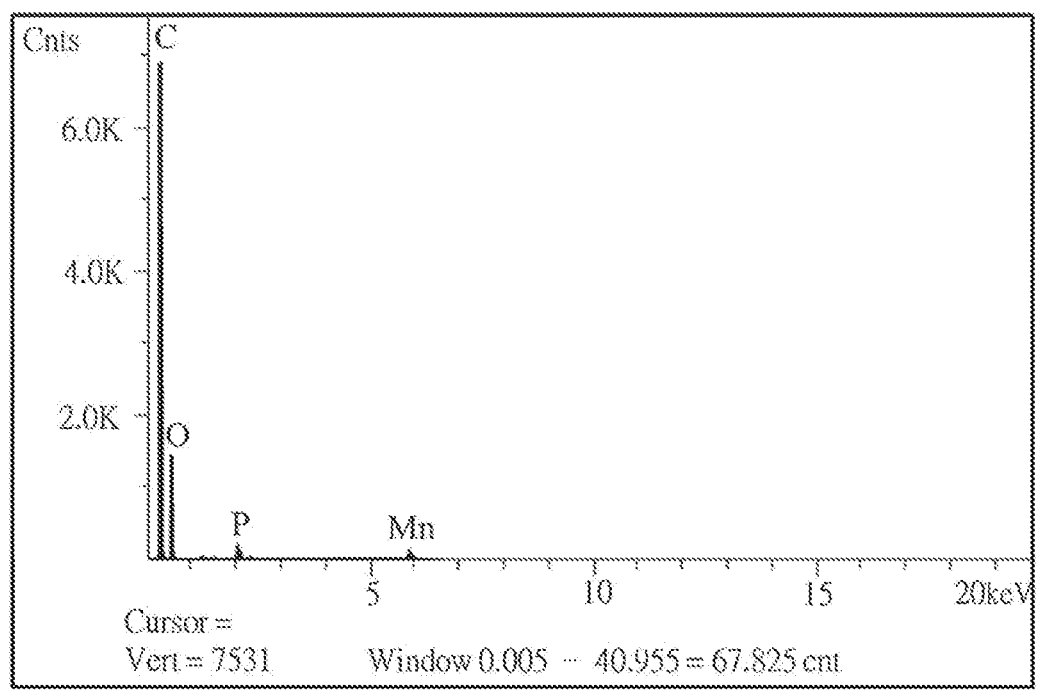

The isolated *Cladosporium* sp. XM01 was inoculated into a Mn$^2$-containing liquid HAY culture medium (inoculum size was 1×10$^5$ conidia/mL); and cultured in the dark for 3 d at 25° C. and 170 rpm to collect biological manganese oxides; the biological manganese oxides were subjected to SEM and EDX. The results of SEM combined with EDX were as shown in FIG. 3 and table 1; marker 1 denoted an aggregate containing manganese oxides; marker 2 denoted manganese oxide-free mycelium surface; higher content of manganese oxides was detected in the marker 1 of the *Cladosporium* sp. XM01 strain cells, being up to 30.81%; compared with marker 2, the manganese content increased by 25.68%. Thus, it can be seen that the strain XM01 could form manganese oxide aggregates on the epispore, and may participate in the manganese oxidation process via protein factors distributed on the epispore.

TABLE 1

EDX results

| | Mass percentage | | Atom percentage | |
|---|---|---|---|---|
| Element | Marker 1 | Marker 2 | Marker 1 | Marker 2 |
| C K$^a$ | 29.90 | 52.52 | 45.89 | 61.59 |
| N K$^a$ | 3.23 | 7.16 | 4.26 | 7.20 |
| O K$^a$ | 32.19 | 32.51 | 37.09 | 28.62 |
| Na K$^a$ | 0.39 | 0.19 | 0.31 | 0.12 |
| Mg K$^a$ | 0.41 | 0.22 | 0.31 | 0.13 |
| Al K$^a$ | 0.39 | 0.22 | 0.26 | 0.11 |
| Si K$^a$ | 0.25 | 0.13 | 0.16 | 0.06 |
| P K$^a$ | 1.57 | 1.32 | 0.93 | 0.60 |
| S K$^a$ | 0.45 | 0.37 | 0.26 | 0.16 |
| K K$^a$ | 0.41 | 0.23 | 0.19 | 0.08 |
| Mn K$^a$ | 30.81 | 5.13 | 10.34 | 1.31 |

Note:
K$^a$ referred to energy excited by an atomic layer K.

Example 4

Studies on Biological Oxidation Properties of the *Cladosporium* sp. XM01 Strain to Mn$^{2+}$ The Mn$^{2+}$ oxidation and adsorption capacity of the manganese-oxidizing fungus (*Cladosporium* sp. XM01) were surveyed in the Mn$^{2+}$-adding HAY medium; it was found that the fungus in this present disclosure had good oxidation and adsorption capacity to Mn$^{2+}$ and could remove soluble Mn$^{2+}$ in the matrix completely within a short time, so that most of the Mn$^{2+}$ were transformed into water-insoluble manganese oxides.

Specific steps were as follows:

(1) Manganese Adsorption and Oxidation Properties of the Fungus in this Present Disclosure at Different Periods of Time The isolated *Cladosporium* sp. XM01 was inoculated into sterilized liquid HAY culture medium (inoculum size was 1×10$^5$ conidia ml$^{-1}$) containing 200 μM Mn$^{2+}$, and cultured at 25° C. and 170 rpm for 3 days in the dark. Samples were taken at specific intervals to measure the concentration of Mn$^{2+}$ remaining in a culture solution and to collect biological manganese oxides; and then adsorption and oxidation capacity of the biological manganese oxides to Mn$^{2+}$ were measured by a two-step extraction method.

Samples of the culture solution were filtered by a 0.45 μm filter membrane, and then the concentration of Mn$^{2+}$ remaining in the culture solution was measured by Inductively Coupled Plasma-Atomic Emission Spectrometry (ICP-AES) (Agilent, 5110 series).

Two-step extraction method: a medium was centrifuged for 10 min at 3000 r/min to collect precipitates (including mycelia and solid-phase manganese oxides); afterwards, the precipitates were washed by deionized water and resuspended by 20 mM copper sulfate for 16 h to extract extracellularly adsorbed Mn$^{2+}$; and then the precipitates were washed by deionized water to thoroughly disrupt cells in the precipitates by a cell disruption method (working for 3 s at 2 h interval for 15 acoustic wave cycles in total), and the disrupted samples were treated by an extracellular adsorption method to extract Mn$^2$ absorbed intracellularly, and finally, treated by 50 mM hydroxylamine hydrochloride to extract the oxidized Mn. The concentration of manganese in the extractive was measured by ICP-AES (Agilent, 5110 series).

Figure 4:
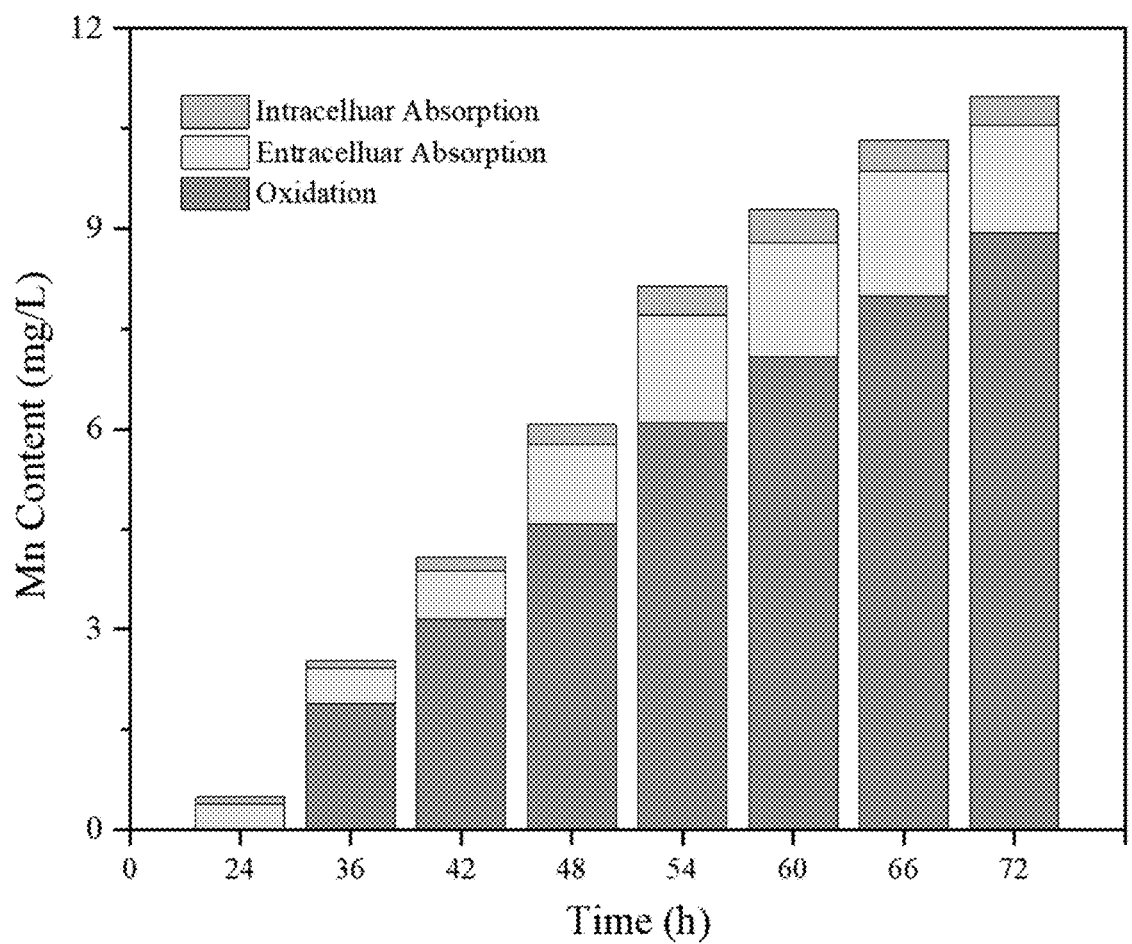
FIG. 4 shows $Mn^{2+}$ adsorption and oxidization properties (initial concentration is 200 μM) of *Cladosporium* sp. XM01 in this present disclosure.

As shown in FIG. 4, the strain was sensitive to the environment and had lower oxidation capacity to manganese after being cultured for 0-24 h; and Mn (II) was mainly removed by extracellular adsorption. After being cultured for 24-48 h, the strain was up to the increased logarithmic phase and achieved a rapid increase in quantity, which was beneficial to adsorption; the adsorption rate was 13.64% at 48 h; and the strain adapted to the environment and had an ability to oxidize manganese. After being cultured for 48-66 h, the adsorption rate increased slowly, and the cell adsorption rate was up to 21.18% at 66 h; while after being cultured for 72 h, Mn (II) in the solution was basically removed, and the adsorption capacity suffered a decrease; and the adsorption rate decreased to 18.63%; this was probably because the strain rapidly increased in the logarithmic phase in quantity, and accordingly the adsorption rate increased rapidly. In a stabilization stage, the adsorption capacity tended to be stable and even decline, resulting in the slow growth of the adsorption rate. After the grain was cultured for 24 h, Mn (II) oxidation enhanced rapidly, and the manganese oxidation rate was up to 81.18% at 72 h. This finding provided that the *Cladosporium* sp. XM01 strain had high manganese oxidation capacity. The adsorption capacity tended to decline at 72 h, while the oxidation capacity was tending to increase. This was the result of oxidizing the adsorbed manganese. In a word, Mn (II) oxidation of the manganese-oxidizing fungus played a leading role in the removal of soluble Mn (II).

EXISTING LITERATURE

1. Zhang Y, Tang Y K, et al. A novel manganese oxidizing bacterium-*Aeromonas hydrophila* strain DS02: Mn(II) oxidization and biogenic Mn oxides generation. Journal of Hazardous Materials, 2019, 367: 539-545.
2. Tang W W, Gong J M, Wu L J, et al. DGGE diversity of manganese mine samples and isolation of a *Lysinibacillus* sp. efficient in removal of high Mn (II) concentrations. Chemosphere, 2016, 165: 277-283.

As shown in Table 2, compared with the manganese oxidizing bacterium reported in the above existing literature, the manganese-oxidizing fungus in this present patent has a manganese removal rate of 99.9%; and the manganese oxidation rate is up to 81.18%; therefore, the manganese-oxidizing fungus of this present disclosure has significant advantages.

TABLE 2

Comparison in manganese removal effect and oxidation effect of different manganese-oxidizing bacteria

| No. | Manganese-oxidizing bacteria | Manganese removal rate | Manganese oxidation rate | Literature |
| --- | --- | --- | --- | --- |
| 1 | *Aeromonas* sp. DS02 | 89.6% | 49.6% | Zhang et al., 2019 |
| 2 | *Lysinibacillus* sp. | 94.7% | 55.9% | Tang et al., 2016 |
| 3 | *Cladosporium* sp. | 99.9% | 81.18% | The present patent |

(2) Manganese Oxidation Properties of the Fungus in this Present Disclosure Under Different Concentrations of $Mn^{2+}$ The $Mn^{2+}$ oxidation capacity of the manganese-oxidizing fungus (*Cladosporium* sp. XM01) in this present disclosure was surveyed in a $Mn^{2+}$-adding medium. It was found that the fungus in this present disclosure had very good oxidation capacity to $Mn^{2+}$, and could completely remove the soluble $Mn^{2+}$ in the matrix within a short time; and most of the $Mn^{2+}$ were transformed into water-insoluble manganese oxides. Through the culture experiments under different initial concentrations of $Mn^{2+}$, it was found that the fungus in this present disclosure could completely remove 800 μM $Mn^{2+}$ and lower; moreover, with the increase of the $Mn^{2+}$ initial concentration, the manganese oxidation activity of the fungus tended to be lower slightly. Specific steps were as follows:

The isolated *Cladosporium* sp. XM01 was inoculated into sterilized liquid HAY culture medium (inoculum size was $1\times10^5$ conidia/mL) containing different concentrations of $Mn^{2+}$, and cultured at 25° C. and 170 rpm in the dark. Samples of the culture solution were taken at specific intervals, and filtered by a 0.45 μm filter membrane, and then the concentration of $Mn^{2+}$ remaining in the culture solution was measured by Inductively Coupled Plasma-Atomic Emission Spectrometry (ICP-AES) (Agilent, 5110 series).

Figure 5:
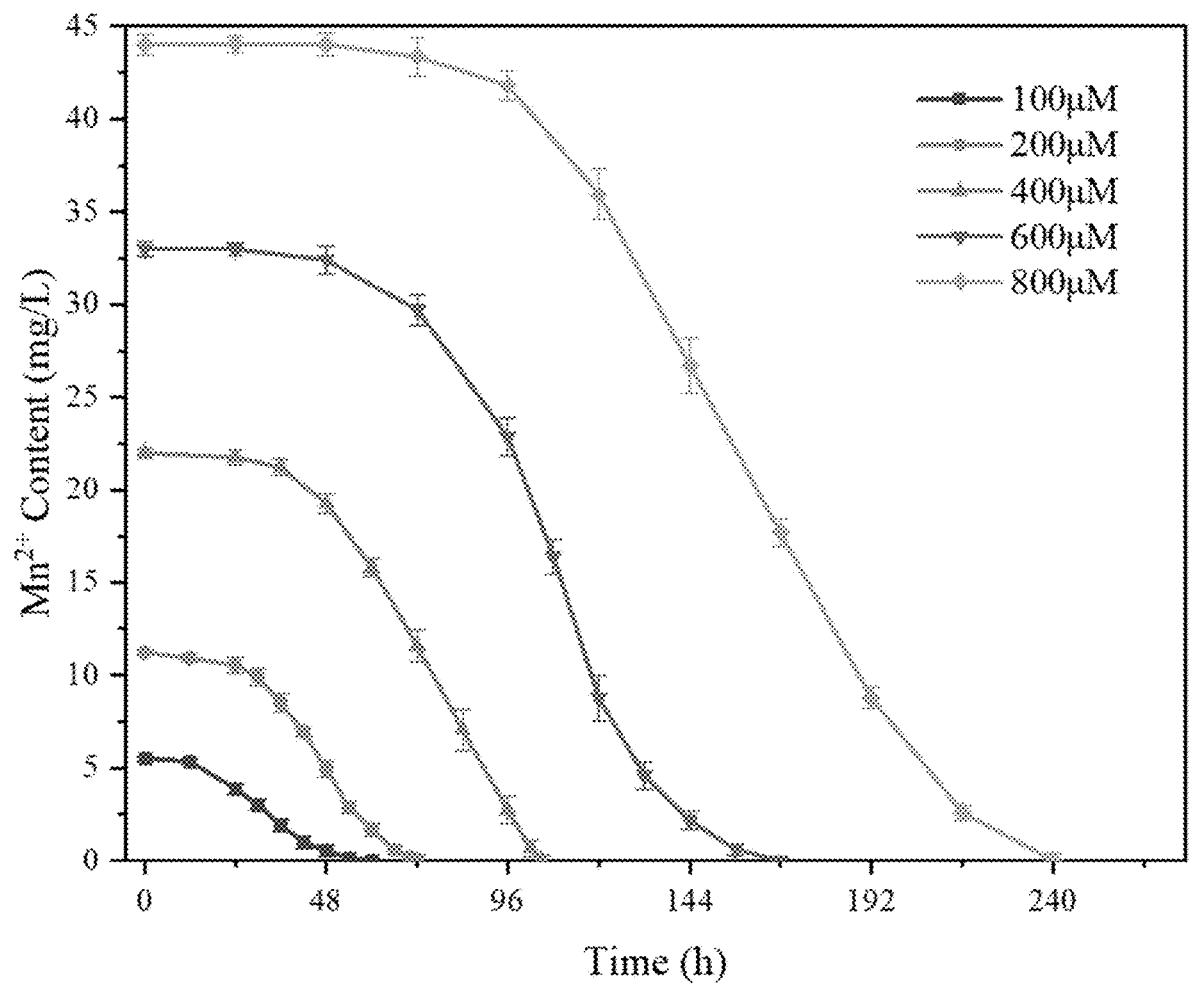
FIG. 5 shows a $Mn^{2+}$ oxidization curve of *Cladosporium* sp. XM01 in this present disclosure at different concentrations of manganese.

As shown in FIG. 5, the fungus could thoroughly remove 800 μM $Mn^{2+}$ and lower; and with the increase of the $Mn^{2+}$ concentration, the manganese oxidation activity of the fungus to $Mn^{2+}$ tended to be lower slightly; but 800 μM concentration of $Mn^{2+}$ has been much greater than the concentration of $Mn^{2+}$ in common rivers or underground water. The results indicate that the fungal flora can thoroughly oxidize the $Mn^{2+}$ within a concentration range in a common water body.

(3) Manganese Oxidation Properties of the Fungus in the Present Disclosure Under Different Temperature Conditions Based on the studies on the manganese oxidation properties of the fungus under different culture temperature, it was found that the fungus in the present disclosure had $Mn^{2+}$ oxidation activity within a temperature range of 15–30° C.; and from the angle of practical application, it was relatively appropriate to choose 20-30° C. Specific steps were as follows:

The isolated *Cladosporium* sp. XM01 was inoculated into sterilized liquid HAY culture medium (inoculum size was $1\times10^5$ conidia/mL), and $Mn^{2+}$ having a final concentration of 200 μM and a 20 mM HEPES buffer solution having a pH value of 7.0 were added in a filtering way; and then respectively placed onto tables in the dark at 170 rpm and 15° C., 20° C., 25° C., and 30° C. Samples of the culture solution were taken at specific intervals, and filtered by a 0.45 μm filter membrane, and then the concentration of $Mn^{2+}$ remaining in the culture solution was measured by Inductively Coupled Plasma-Atomic Emission Spectrometry (ICP-AES) (Agilent, 5110 series).

Figure 6:
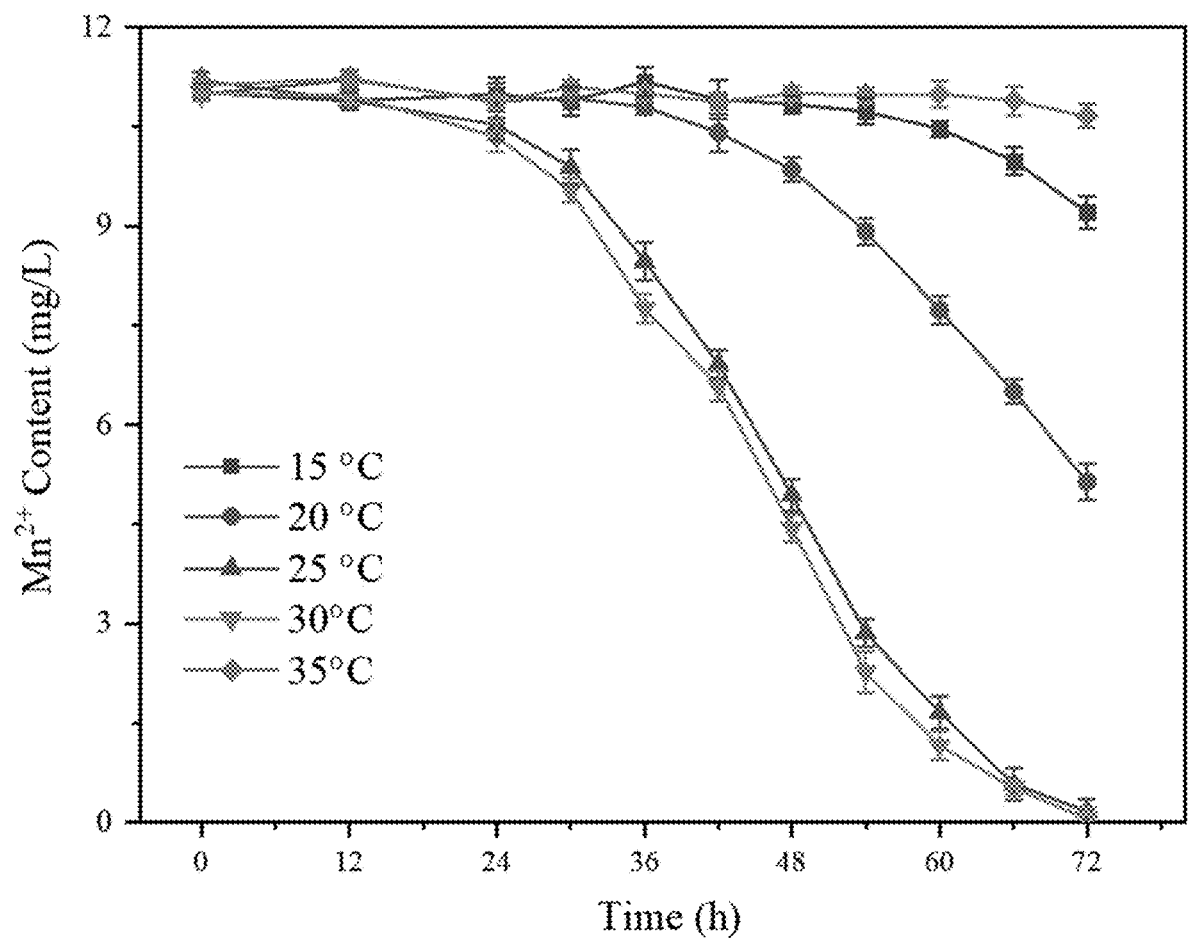
FIG. 6 shows $Mn^{2+}$ oxidation activity of *Cladosporium* sp. XM01 in this present disclosure at different temperature.

As shown in FIG. 6, the manganese oxidation activity of the fungus decreased with the decrease of the culture temperature; and the oxidation rate was the slowest at 15° C., and faster slightly at 20° C., and up to the maximum at 25-30° C. It indicates that the most suitable oxidizing temperature of the fungus was in a range from 25 to 30° C. The fungus can exert manganese oxidation activity at a low temperature of 15° C., showing its stronger adaptability to the temperature.

(4) Manganese Oxidation Properties of the Fungus in the Present Disclosure Under Different pH Conditions Through the oxidation experiments at different initial pH values, it was found that the most suitable pH for manganese oxidation of the fungus was 7; and the specific steps were as follows:

The isolated *Cladosporium* sp. XM01 was inoculated into sterilized liquid HAY culture medium (inoculum size was $1\times10^5$ conidia/mL), and $Mn^{2+}$ having a final concentration of 200 μM was added in a filtering way; and then pH was respectively adjusted to 6 and 6.5 by an MES buffer solution; then the pH was respectively adjusted to 7.0 and 7.5 by an HEPES buffer solution; and cultured on a table at 170 rpm in the dark. Samples of the culture solution were taken at specific intervals, and filtered by a 0.45 μm filter membrane, and then the concentration of $Mn^{2+}$ remaining in the culture solution was measured by Inductively Coupled Plasma-Atomic Emission Spectrometry (ICP-AES) (Agilent, 5110 series).

Figure 7:
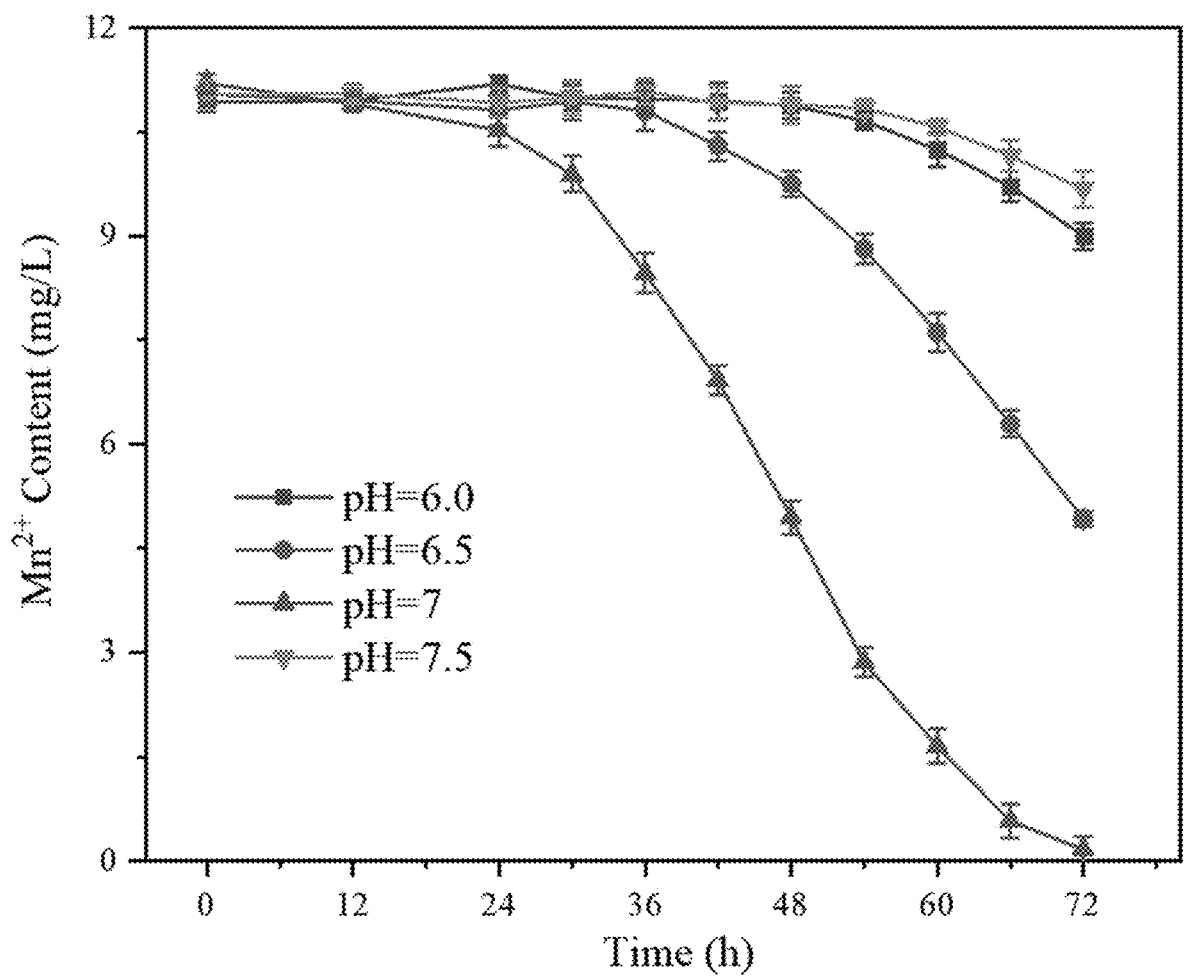
FIG. 7 shows $Mn^{2+}$ oxidation activity of *Cladosporium* sp. XM01 in this present disclosure at different pH values.

As shown in FIG. 7, the manganese oxidation rate was up to the maximum at pH=7; the fungus could basically oxidize $Mn^{2+}$ within a pH range of 6.0-7.5; moreover, the pH range is consistent with the pH of most of the water bodies in natural world, indicating that the fungus can exert manganese oxidation activity under pH conditions of the natural water body.

To sum up, researchers found that the *Cladosporium* sp. XM01 had $Mn^{2+}$ oxidation activity within a pH range of 6.0-7.5 and a temperature range of 15–30° C., and had $Mn^{2+}$ oxidation activity under the condition that $Mn^2$ concentration was not higher than 800 μM.

The above description made to the examples is convenient for those skilled in the art to understand and use the present disclosure. Apparently, those skilled in the art can readily make various amendments to these examples, and apply the general principles described herein to other examples without any inventive labor. Therefore, the present disclosure is not limited to the above examples; based on the present disclosure, improvements and amendments made by those skilled in the art without departing from the spirit and scope of the present disclosure shall fall within the protection scope of the present disclosure.

What is claimed is:

1. A method for removing Mn$^{2+}$ from a water body or a solid matrix, the method comprising the following steps of:

inoculating a manganese-oxidizing fungus or a microbial agent comprising the manganese-oxidizing fungus into the water body or the solid matrix; and culturing for a predetermined period of time under conditions of 25-30° C. and pH 7.0, so that the Mn$^{2+}$ is transformed into a manganese oxide, wherein the manganese-oxidizing fungus is *Cladosporium* sp. XM01, which has been preserved in China General Microbiological Culture Collection Center (accession number: CGMCC NO. 21083).

2. The method for removing Mn$^{2+}$ from the water body or the solid matrix according to claim 1, wherein the water body comprises industrial wastewater, domestic wastewater, underground water and tap water; and the solid matrix comprises a soil and a sediment.

\* \* \* \* \*